(12) United States Patent
Butler et al.

(10) Patent No.: US 9,272,962 B2
(45) Date of Patent: Mar. 1, 2016

(54) METHOD FOR PRODUCTION OF STYRENE FROM TOLUENE AND METHANOL

(71) Applicant: FINA TECHNOLOGY, INC., Houston, TX (US)

(72) Inventors: James R. Butler, Spicewood, TX (US); Joseph E. Pelati, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 0 days.

(21) Appl. No.: 14/626,746

(22) Filed: Feb. 19, 2015

(65) Prior Publication Data

US 2015/0158793 A1  Jun. 11, 2015

Related U.S. Application Data

(63) Continuation of application No. 14/299,395, filed on Jun. 9, 2014, now Pat. No. 9,012,708, which is a continuation of application No. 14/093,667, filed on Dec. 2, 2013, now Pat. No. 8,796,498, which is a continuation of application No. 12/345,550, filed on Dec. 29, 2008, now Pat. No. 8,686,205.

(51) Int. Cl.
| | |
|---|---|
| *C07C 1/20* | (2006.01) |
| *C07C 2/86* | (2006.01) |
| *C07C 15/46* | (2006.01) |
| *C07C 45/00* | (2006.01) |
| *C07C 45/38* | (2006.01) |
| *C07C 1/207* | (2006.01) |
| *C07C 45/32* | (2006.01) |

(52) U.S. Cl.
CPC ............... *C07C 2/867* (2013.01); *C07C 1/2076* (2013.01); *C07C 15/46* (2013.01); *C07C 45/002* (2013.01); *C07C 45/32* (2013.01); *C07C 45/38* (2013.01); *C07C 2521/04* (2013.01); *C07C 2521/06* (2013.01); *C07C 2521/08* (2013.01); *C07C 2523/02* (2013.01); *C07C 2523/04* (2013.01); *C07C 2523/06* (2013.01); *C07C 2523/10* (2013.01); *C07C 2523/20* (2013.01); *C07C 2523/22* (2013.01); *C07C 2523/24* (2013.01); *C07C 2523/34* (2013.01); *C07C 2523/42* (2013.01); *C07C 2523/44* (2013.01); *C07C 2523/46* (2013.01); *C07C 2523/72* (2013.01); *C07C 2523/75* (2013.01); *C07C 2523/755* (2013.01); *C07C 2523/80* (2013.01); *C07C 2523/86* (2013.01); *C07C 2527/047* (2013.01); *C07C 2527/049* (2013.01); *C07C 2527/051* (2013.01); *C07C 2529/06* (2013.01); *C07C 2529/40* (2013.01)

(58) Field of Classification Search
CPC .............................. C07C 1/2076; C07C 2/867
USPC .................................. 585/437, 313, 319, 323
See application file for complete search history.

(56) References Cited

U.S. PATENT DOCUMENTS 4,479,024 A * 10/1984 Bruylants ............... C07C 2/867
                                                                      502/340

* cited by examiner

*Primary Examiner* — Thuan D Dang
(74) *Attorney, Agent, or Firm* — Albert Shung

(57) ABSTRACT

A process is disclosed for making styrene by converting methanol to formaldehyde in a reactor then reacting the formaldehyde with toluene to form styrene in a separate reactor.

17 Claims, 2 Drawing Sheets

METHOD FOR PRODUCTION OF STYRENE FROM TOLUENE AND METHANOL

CROSS-REFERENCE TO RELATED APPLICATIONS

This application is a Continuation of U.S. application Ser. No. 14/299,395, filed on Jun. 9, 2014, which is a Continuation of U.S. application Ser. No. 14/093,667, filed on Dec. 2, 2013, now issued as U.S. Pat. No. 8,796,498, which is a Continuation of U.S. application Ser. No. 12/345,550, filed on Dec. 29, 2008, now issued as U.S. Pat. No. 8,686,205.

FIELD

The present invention relates to a method for the production of styrene.

BACKGROUND

Styrene is an important monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3 + H_2 \rightarrow C_6H_6 + CH_4$. This reaction requires energy input and as can be seen from the above equation, produces methane as a byproduct, which is typically separated and may used as heating fuel for the process.

In view of the above, it would be desirable to have a process of producing styrene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams.

SUMMARY

An embodiment of the present invention is a process for making styrene by converting methanol to formaldehyde in one or more first reactors to form a first product stream comprising formaldehyde and reacting the formaldehyde with toluene in one or more second reactors to form a second product stream comprising styrene. The first product stream can include one or more of hydrogen, water, or methanol. The methanol, if any is present, can be separated from the first product stream and recycled to the one or more first reactors.

The process can include utilizing one or more oxidation reactors to convert methanol into formaldehyde and water to form the first product stream. The process can optionally include utilizing one or more dehydrogenation reactors to convert methanol into formaldehyde and hydrogen to form the first product stream.

The second product stream can include one or more of toluene, water, or formaldehyde. The toluene and/or formaldehyde, if any is present, can be separated from the second product stream and recycled to the one or more second reactors. The one or more second reactors can include a reaction zone under reaction conditions containing a catalyst for reacting toluene and formaldehyde to form styrene. The process can include passing the first product stream to a separation stage for separating formaldehyde from the first product stream. The separation stage can comprise a membrane separation capable of removing hydrogen from the formaldehyde stream.

Another embodiment of the present invention is a process for making styrene by converting methanol to formaldehyde in one or more first reactors to form a first product stream comprising one or more of formaldehyde, hydrogen, water, or methanol. The first product stream proceeds to a first separation stage for separating formaldehyde from the first product stream. The separation stage can include a membrane separation unit capable of removing hydrogen from the formaldehyde stream prior to the second reactor.

Toluene and formaldehyde are reacted in one or more second reactors to form a second product stream comprising one or more of styrene, toluene, water, or formaldehyde. The second product stream then passes to a second separation stage for separating styrene from the second product stream. Methanol, of present, can be separated from the first product stream and recycled to the one or more first reactors. Toluene and formaldehyde, if present, can be separated from the second product stream and recycled to the one or more second reactors.

The process can include utilizing one or more oxidation reactors to convert methanol into formaldehyde and water to form the first product stream. The process can optionally include utilizing one or more dehydrogenation reactors to convert methanol into formaldehyde and hydrogen to form the first product stream. The one or more second reactors can comprise a reaction zone under reaction conditions containing a catalyst for reacting toluene and formaldehyde to form styrene. The catalyst can be a basic or neutral catalyst, and can be a basic or neutral zeolite catalyst. The catalyst can comprise one or more promoters chosen from the group of alkali elements, alkaline earth elements, rare earth elements, Y, Zr, and Nb.

DETAILED DESCRIPTION

Figure 1:
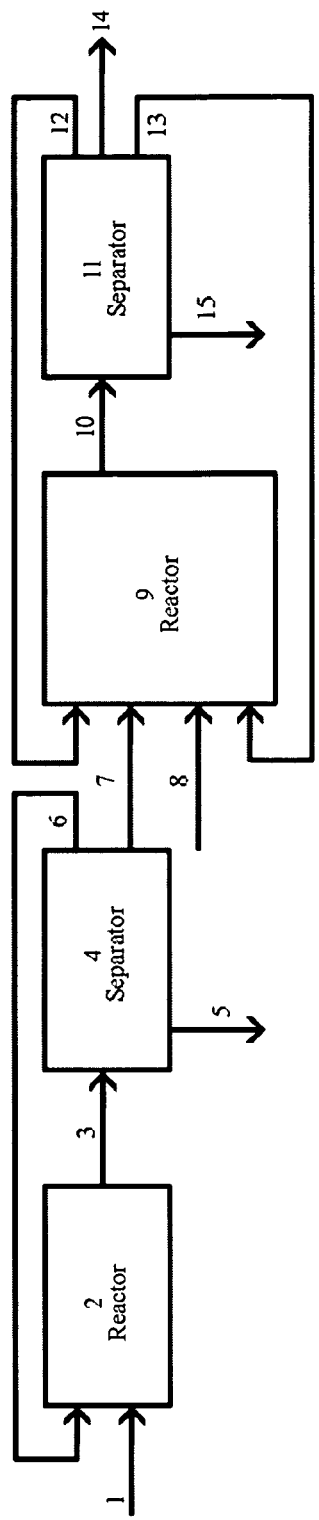
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

Toluene has been used to produce styrene by reactions with either methanol or methane/oxygen as the co-feed. Theoretically methanol ($CH_3OH$) and toluene ($C_6H_5CH_3$) can be reacted together to form styrene, water and hydrogen gas, as shown below:

$$CH_3OH + C_6H_5CH_3 \rightarrow C_8H_8 + H_2O + H_2$$

In practice, however, the methanol ($CH_3OH$) often dehydrogenates into formaldehyde ($CH_2O$) and hydrogen gas ($H_2$). Often the toluene conversion is low or the selectivity to products of the methanol is too low to make the process economical. Conversion of methanol to COx or methane can result in an undesirable by-product stream that is not easily recovered. In order to avoid this undesirable side reaction, a method of producing styrene utilizing a separate reactor to convert methanol into formaldehyde is disclosed. Toluene can then be reacted directly with formaldehyde to produce styrene and water. This process avoids the instability aspects of the methanol.

Formaldehyde can be produced either by the oxidation or dehydrogenation of methanol. Silver-based catalysts are most commonly used for this process but copper can also be used. Iron-molybdenum-oxide catalysts are typically used for the dehydrogenation route. A separate process for the dehydrogenation or oxidation of methanol into formaldehyde gas could be utilized.

A separation unit may then be used if needed in order to separate the formaldehyde from the hydrogen gas or water from the formaldehyde and unreacted methanol prior to reacting it with toluene for the production of styrene. This separation would inhibit the hydrogenation of the formaldehyde back to methanol. Purified formaldehyde could then be sent to the second reactor and the unreacted methanol could be recycled. The use of formaldehyde for the side chain alkylation of toluene is shown below:

$$CH_2O + C_6H_5CH_3 \rightarrow C_8H_8 + H_2O$$

Formaldehyde can be produced by the oxidation of methanol to produce formaldehyde and water. The oxidation of methanol is described in the equation below:

$$2CH_3OH + O_2 \rightarrow 2CH_2O + 2H_2O$$

Alternately formaldehyde can be produced by the dehydrogenation of methanol to produce formaldehyde and hydrogen gas. This method produces a dry formaldehyde stream that may be preferred as it would not require the separation of the water prior to the reaction of the formaldehyde with toluene. The dehydrogenation process is described in the equation below:

$$CH_3OH \rightarrow CH_2O + H_2$$

In order to prevent the hydrogenation of formaldehyde back to methanol, it is desirable to have the separation of formaldehyde from either water or hydrogen gas prior to its reaction with toluene. Separating the formaldehyde from the other byproducts of the oxidation or dehydrogenation reaction would result in a stable formaldehyde stream that could be used in the production of styrene.

Although the reaction has a 1:1 molar ratio of toluene and formaldehyde, the ratio of the feedstreams is not limited within the present invention and can vary depending on operating conditions and the efficiency of the reaction system. If excess toluene or formaldehyde is fed to the reaction zone, the unreacted portion can be subsequently separated and recycled back into the process. In one embodiment the ratio of toluene: formaldehyde can range from between 100:1 to 1:100. In alternate embodiments the ratio of toluene:formaldehyde can range between from 50:1 to 1:50; from 20:1 to 1:20; from 10:1 to 1:10; from 5:1 to 1:5; from 2:1 to 1:2.

In FIG. 1 there is a simplified flow chart of one embodiment of the styrene production process described above. The first reactor (2) is either a dehydrogenation reactor or an oxidation reactor. This reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the clean formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) comprising formaldehyde and water. The product stream (3) comprising formaldehyde and water can then be sent to the second reactor (9) without a separation unit (4).

The formaldehyde feed stream (7) is then reacted with a feed stream of toluene (8) in the second reactor (9). The toluene and formaldehyde react to produce styrene. The product (10) of the second reactor (9) may then be sent to an optional separation unit (11) where any unwanted byproducts (15) such as water can separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if required.

The operating conditions of the reactors and separators will be system specific and can vary depending on the feedstream composition and the composition of the product streams. The reactor (9) for the reaction of toluene and formaldehyde will operate at elevated temperatures and pressures, such as for a non-limiting example from 250° C. to 750° C. and from 1 atm to 70 atm in pressure and may contain a basic or neutral catalyst system.

Suitable catalysts for the reaction of toluene and formaldehyde can include as non-limiting examples metal oxides such as: CuO; ZnO—CuO; ZnO—CuO—$Al_2O_3$; $CuCr_2O3$; $ZnCr_2O_3$; or ZnO—CuO—$Cr_2O_3$. Other catalysts that can be used include metals supported on a substrate such as silica or titania, for example: Ru; Rh; Ni; Co; Pd; or Pt. These can also contain promoters such as Mn, Ti, Zr, V, Nb, K, Cs, or Na. Still another group of catalysts that can be used for the present invention include sulfide based catalysts such as: $MoS_2$; $WS_2$; $Mo_2WS_2$; $CoMoS_2$; or $NoMoS_2$. These sulfide catalysts can include promoters such as K, Rb, Cs, Ca, Sr, Ba, La, or Ce.

The above catalysts can have toluene promoters added such as the alkali, alkaline earth, and/or rare earth elements. Other toluene promoters that can be added include Y, Zr, and/or Nb.

Improvement in side chain alkylation selectivity may be achieved by treating a molecular sieve zeolite catalyst with proper chemical compounds to inhibit the external acidic sites and minimize aromatic alkylation on the ring positions. Another means of improvement of side chain alkylation selectivity can be to impose restrictions on the catalyst structure to facilitate side chain alkylation. In one embodiment the catalyst used in an embodiment of the present invention is a basic or neutral catalyst.

The catalytic reaction systems suitable for this invention can include one or more of the zeolite or amorphous materials modified for side chain alkylation selectivity. A non-limiting example can be a zeolite promoted with one or more of the following: Ru, Rh, Ni, Co, Pd, Pt, Mn, Ti, Zr, V, Nb, K, Cs, or Na.

Zeolite materials suitable for this invention may include silicate-based zeolites and amorphous compounds such as faujasites, mordenites, pentasils, etc. Silicate-based zeolites are made of alternating $SiO_2$ and $MO_x$ tetrahedra, where M is an element selected from the Groups 1 through 16 of the Periodic Table (new IUPAC). These types of zeolites have 8-, 10-, or 12-membered oxygen ring channels. An example of zeolites of this invention can include 10- and 12-membered ring zeolites, such as ZSM-5, ZSM-11, ZSM-22, ZSM-48, ZSM-57, etc.

Figure 2:
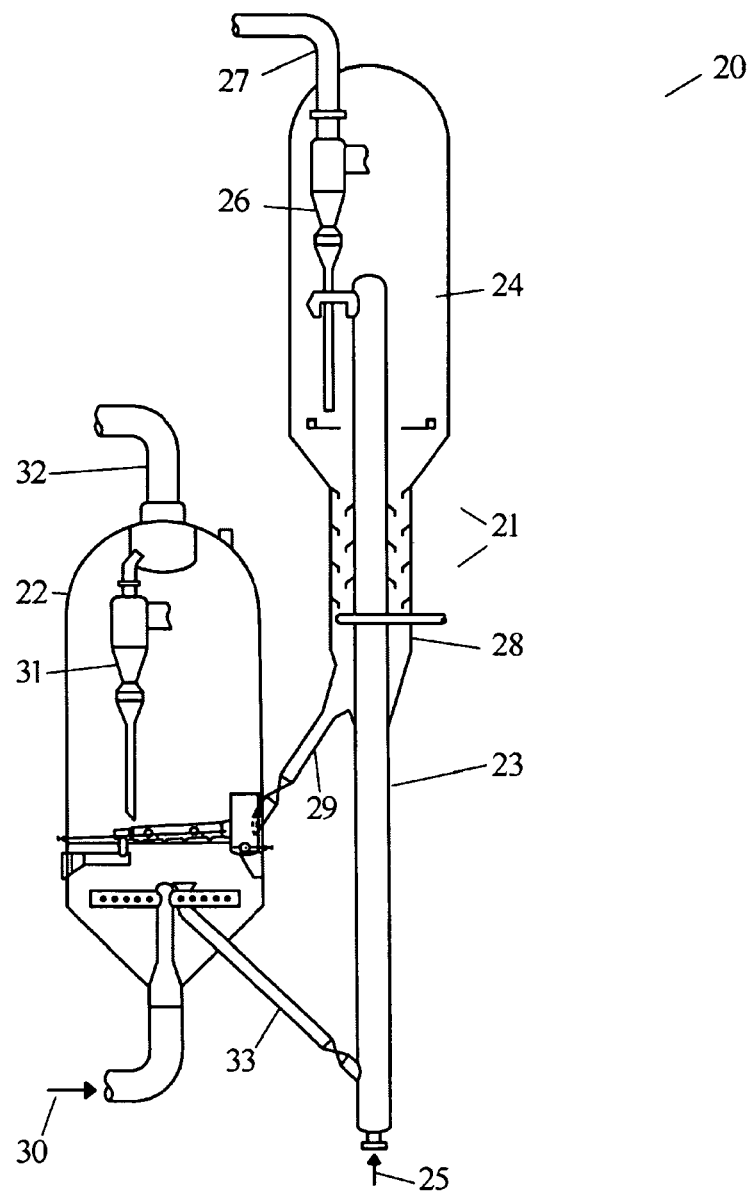
FIG. 2 is a schematic illustration of an aspect of an embodiment of the present invention having the capability for continuous reaction with catalyst regeneration.

Embodiments of reactors that can be used with the present invention can include, by non-limiting examples: fixed bed reactors; fluid bed reactors; and entrained bed reactors. Reactors capable of the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention. An example of a fluid bed reactor having catalyst regeneration capabilities that may be employed with the present invention is illustrated in FIG. 2. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line (not shown) or adding new catalyst into the system while in operation.

FIG. 2 is a schematic illustration of an aspect of an embodiment of the present invention having the capability for continuous reaction with catalyst regeneration. The reaction process (20) generally comprises two main zones for reaction (21) and regeneration (22). A reaction zone can be comprised of a vertical conduit, or riser (23), as the main reaction site, with the effluent of the conduit emptying into a large volume process vessel, which may be referred to as a separation vessel (24). In the reaction riser (23), a feed stream (25), such as toluene and formaldehyde, is contacted with a fluidized catalyst, which can be a relatively large fluidized bed of catalyst, at reactor conditions. The residence time of catalyst and hydrocarbons in the riser (23) needed for substantial completion of the reaction may vary as needed for the specific reactor design and throughput design. The flowing vapor/catalyst stream leaving the riser (23) may pass from the riser to a solids-vapor separation device, such as a cyclone (26), normally located within and at the top of the separation vessel (24). The products of the reaction can be separated from the portion of catalyst that is carried by the vapor stream by means of one or more cyclone (26) and the products can exit the cyclone (26) and separation vessel (24) via line (27). The spent catalyst falls downward to a stripper (28) located in a lower part of the separation vessel (24). Catalyst can be transferred to a regeneration vessel (22) by way of a conduit (29) connected to the stripper (28).

The catalyst can be continuously circulated from the reaction zone (21) to the regeneration vessel (22) and then again to the reaction zone (21). The catalyst can therefore act as a vehicle for the transfer of heat from zone to zone as well as providing the necessary catalytic activity. Catalyst from the reaction zone (21) that is being transferred to the regeneration zone (22) can be referred to as "spent catalyst". The term "spent catalyst" is not intended to be indicative of a total lack of catalytic activity by the catalyst particles. Catalyst, which is being withdrawn from the regeneration vessel (22), is referred to as "regenerated" catalyst. The catalyst can be regenerated in the regeneration vessel (22) by heat and contact with a regeneration stream (30). The regeneration stream (30) can comprise oxygen and can comprise steam. The regenerated catalyst can be separated from the regeneration stream by the use of one or more cyclones (31) that can enable the removal of the regeneration vessel (22) via line (32). The regenerated catalyst can be transferred via line (33) to the lower section of the riser (23) where it is again in contact with the feed stream (25) and can flow up the riser (23).

Use of broader terms such as comprises, includes, having, etc. should be understood to provide support for narrower terms such as consisting of, consisting essentially of, comprised substantially of, etc.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "spent catalyst" refers to a catalyst that has lost enough catalyst activity to no longer be efficient in a specified process. Such efficiency is determined by individual process parameters.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A process for making styrene comprising:
reacting toluene and formaldehyde in one or more reactors over a metal supported on a substrate to form a product stream comprising styrene, wherein the substrate comprises silica or titania, and wherein the metal comprises Ru, Rh, Ni, Co, Pd or Pt.

2. A process for making styrene comprising:
converting methanol to formaldehyde in one or more first reactors to form a first product stream comprising formaldehyde;
passing the first product stream to a separation stage for separating formaldehyde from the first product stream; and
reacting toluene and formaldehyde in one or more second reactors over a catalyst comprising a metal supported on a substrate to form a second product stream comprising styrene, wherein the substrate comprises silica or titania, and wherein the metal comprises Ru, Rh, Ni, Co, Pd or Pt.

3. The process of claim 2, wherein the catalyst is promoted with Mn, Ti, Zr, V, Nb, K, Cs or Na.

4. The process of claim 2, wherein the catalyst includes one or more promoters selected from alkali elements, alkaline earth elements, and rare earth elements.

5. The process of claim 2, wherein the catalyst includes one or more promoters selected from a group consisting of Y, Zr, Nb, and combinations thereof.

6. The process of claim 2, wherein the catalyst is basic or neutral.

7. The process of claim 2, wherein the toluene is reacted with the formaldehyde at a temperature ranging from 250° C. to 750° C.

8. The process of claim 2, wherein the toluene is reacted with the formaldehyde at a pressure ranging from 1 atm to 70 atm.

9. The process of claim 2, wherein the first product stream further comprises one or more of hydrogen, water, or methanol.

10. The process of claim 2, wherein methanol is separated from the first product stream and recycled to the one or more first reactors.

11. The process of claim 2, further comprising utilizing one or more oxidation reactors to convert methanol into formaldehyde and water to form the first product stream.

12. The process of claim 2, further comprising utilizing one or more dehydrogenation reactors to convert methanol into formaldehyde and hydrogen to form the first product stream.

13. The process of claim 2, wherein the second product stream further comprises one or more of toluene, water, or formaldehyde.

14. The process of claim 2, further comprising passing the second product stream to a second separation stage for separating styrene from the second product stream.

15. The process of claim 14, wherein toluene is separated from the second product stream and recycled to the one or more second reactors.

16. The process of claim 15, wherein formaldehyde is separated from the second product stream and recycled to the one or more second reactors.

17. The process of claim 2, wherein the first separation stage comprises a membrane to remove hydrogen from the first product stream.

* * * * *